United States Patent [19]

Foster et al.

[11] 4,442,077

[45] Apr. 10, 1984

[54] METHOD OF REMOVING HYDRIDES OF PHOSPHORUS, ARSENIC, ANTIMONY AND BISMUTH FROM HYDROCARBON AND NON-HYDROCARBON STREAMS

[75] Inventors: David I. Foster, Lake Charles, La.; Paul T. Scott; Mark W. Pierick, both of Corpus Christi, Tex.; Clarence L. Shaddock, Jr., Lake Charles, La.

[73] Assignee: Chemical Engineering Technology, Inc., Lake Charles, La.

[21] Appl. No.: 423,796

[22] Filed: Sep. 27, 1982

[51] Int. Cl.$^3$ .............................................. B01D 53/34
[52] U.S. Cl. ................................. 423/210; 208/253; 208/288
[58] Field of Search ........... 423/210 R, 210 M, 210 S, 423/230, 234; 208/253, 288

[56] References Cited

U.S. PATENT DOCUMENTS

| | | | |
|---|---|---|---|
| 2,313,022 | 3/1943 | Rottmayr | 423/210 R |
| 3,833,498 | 9/1974 | Stahfeld | 208/253 |
| 4,048,387 | 9/1977 | Lahme et al. | 423/210 X |
| 4,063,899 | 12/1977 | Cherow et al. | 55/233 X |
| 4,088,734 | 5/1978 | Gadelle et al. | 423/210 |
| 4,175,111 | 11/1979 | Munday et al. | 423/210 |

*Primary Examiner*—Earl C. Thomas
*Attorney, Agent, or Firm*—John W. Carpenter

[57] ABSTRACT

Method for removing a hydride of an element selected from the group consisting of phosphorous, arsenic, antimony, bismuth, or mixtures thereof, from a hydrocarbon stream, a gas stream, or a mixture of the two streams by initially reducing the free water concentration of the stream or streams or raising the temperatures of the same and subsequently contacting the essentially moisture free effluent with soda lime.

13 Claims, No Drawings

METHOD OF REMOVING HYDRIDES OF PHOSPHORUS, ARSENIC, ANTIMONY AND BISMUTH FROM HYDROCARBON AND NON-HYDROCARBON STREAMS

BACKGROUND OF THE INVENTION

1. Field of the Invention

This invention is related to a method for removing a hydride of an element selected from the group consisting of phosphorous, arsenic, antimony, bismuth, or mixtures thereof. More specifically, this invention provides a method for removing arsine from a petroleum hydrocarbon stream, or a non-hydrocarbon gas stream, or a mixture of the two streams.

2. Description of the Prior Art

Refinery streams used in the production of olefins, such as ethylene and propylene, typically are streams of $C_1$-$C_5$ hydrocarbons and hydrogen and gases containing carbon dioxide, hydrogen sulfide, water, arsine, carbonyl and other undesirable elements and compounds. The arsine is a contaminant which is particularly undesirable in the olefin production process because of its toxicity for the palladium catalyst used in the acetylene convertor. Also, arsine's presence in the olefin product can be undesirable. Thus, it has become important to find a means for removing arsine from hydrocarbon streams. The use of molecular sieves, activated charcoal, bauxite, caustic solutions, slaked lime and other materials known to be effective in the removing of arsine from air, nitrogen, etc., did not solve the problem.

U.S. Pat. No. 4,063,899 by Cheron et al. teaches a device comprising a filtering cartridge of soda-lime which is capable of removing carbon dioxide from a gas flow. U.S. Pat. No. 4,088,734 by Gadelle et al. discloses a process for removing arsenic compounds, and particularly arsine, from gases containing the same. The gases are treated with a washing solution consisting either of an alkaline aqueous solution, containing a zinc or lead salt or oxide and/or one or more salts of anthraquinone sulfonic or disulfonic acids, or of a solution in an organic solvent of at least one quinone compound in the presence of an amine or an ethanol amine. None of the foregoing patents, nor any other prior art, teach or suggest the method for removing arsine from a petroleum hydrocarbon stream, a non-hydrogen gas stream, or a mixture of the two streams.

SUMMARY OF THE INVENTION

It is therefore an object of this invention to provide a method for removing arsine from a petroleum hydrocarbon stream primarily having $C_1$-$C_5$ hydrocarbons and hydrogen.

It is another object of this invention to provide a method for removing a hydride of an element selected from the group consisting of phosphorous, arsenic, antimony, bismuth, or mixtures thereof, from a petroleum hydrocarbon stream primarily having $C_1$-$C_5$ hydrocarbons and hydrogen, or a non-hydrocarbon gas stream including Group O gases, nitrogen, oxygen, carbon monoxide and air, or a mixture of the petroleum hydrocarbon stream and the gas stream.

Still, other objects will be apparent to those skilled in the art from the following description of this invention.

The foregoing objects are achieved according to the practice of the invention. Broadly, this invention comprises a method for removing a hydride of an element selected from the group consisting of phosphorous, arsenic, antimony, bismuth, or mixtures thereof, from a petroleum hydrocarbon stream; or from a non-hydrocarbon gas stream including a gas selected from the group consisting of nitrogen, oxygen, carbon monoxide, air, and a gas or gases of Group O, or mixture of the gases thereof; or a mixture of the hydrocarbon stream and the non-hydrocarbon gas stream. The method further includes the steps of reducing the free water concentration of the hydrocarbon stream or the non-hydrocarbon gas stream or the mixture of the two streams.

DETAILED DESCRIPTION OF THE INVENTION

This invention includes a method which utilizes soda lime for removing a hydride of an element selected from the group consisting of phosphorous, arsenic, antimony, bismuth, or mixtures thereof, from a petroleum hydrocarbon stream or from a non-hydrocarbon gas stream or from a mixture of the two streams. The hydrides of phosphorous, arsenic, antimony and bismuth are respectively better known as phosphine, arsine, stibine and bismuthine. The petroleum hydrocarbon stream is in a gaseous state and includes vaporized liquids and preferably comprises hydrocarbons having between one and five carbon atoms and hydrogen. The non-hydrocarbon gas stream may preferably include a gas selected from the group consisting of nitrogen, oxygen, carbon monoxide, air, and a gas or gases of Group O, or a mixture of the gases thereof.

The stream of gaseous vaporized liquid petroleum hydrocarbon or the non-hydrocarbon gas stream, or the mixture of the two streams, having the phosphine, arsine, stibine or bismuthine, or mixtures of the same, preferably has a flow rate of between about 150 lbs/hr./sq. ft. of soda lime bed and about 450 lbs/hr./sq. ft. of soda lime bed with a pressure of between about 125 lbs/sq. inch absolute and 200 lbs/sq. inch. absolute. The depth of the soda lime bed is critical. We have discovered that the soda lime bed depth has to be at least five (5) feet. Preferably, the soda lime bed depth is eight (8) feet. It may have any maximum length; however, economics would dictate a reasonable maximum length.

Prior to contacting the petroleum hydrocarbon stream, or the non-hydrocarbon gas stream, or the mixture of the two stream, with soda lime in order to remove the phosphine, arsine, stibine, bismuthine or a mixture of the foregoing, the free water concentration within any of the streams or mixture of streams, which is normally within the range of 100 ppm and 1000 ppm, should be preferably reduced to a range of between about 1 ppm to 20 ppm or in the alternative, the temperature of the stream or streams should be increased between 30° F. and 40° F.

In operation of the invention, the preferred means of reducing the free water concentration is pass it through a vapor dryer. Alternatively, if a vapor dryer is not utilized to remove moisture, then the temperature of the gaseous vaporized liquid petroleum hydrocarbon stream or the non-hydrocarbon gas stream, or the mixture of the two streams, has to be elevated to between about 120° F. and about 170° F., or to a temperature of between 30° F. and 40° F. above the water and/or petroleum hydrocarbon or non-hydrocarbon gas stream dew point.

After the free water concentration from the stream or streams, as previously defined, is reduced by the vapor dryer to within 1 ppm to 20 ppm, the relatively moisture free effluent is contacted with soda lime. If, however, the vapor dryer is not utilized to remove the free water concentration, and the temperature of the stream or streams is merely elevated, then the elevated temperature stream or streams is contacted with the soda lime because the stream or streams temperature is above the water and/or petroleum hydrocarbon or non-hydrocarbon gas stream dew point.

The soda lime is generally utilized as a column in a tower formation. It is preferably a a granular solid having a particle size of between about 4 to 8 mesh and consisting essentially of a hydrated mixture of calcium hydroxide and sodium hydroxide, with a moisture content on a wet basis of about 16% or less. It is manufactured by slaking quick lime with a solution of sodium hydroxide, followed by drying by heat. The soda lime may also be in a slurry state. If it is a slurry state, between about 1 wt% and 25 wt% of a compound selected from the group consisting of potassium nitrite and sodium nitrite, or a mixture thereof, is added to the slurry soda lime.

The contact time between the relatively moisture free or elevated temperature hydrocarbon gas or non-hydrocarbon gas, or the mixture of the two, effluent has to be at least 8 seconds. The maximum contact time may be any time within reason (e.g. 2 minutes). More preferably the contact time is about 12 seconds. The contact time depends on the length of the column of solid soda lime through which the stream or streams is passed, or, in the case of aqueous soda lime, the length of the column of liquid soda lime through which the stream or streams is percolated in order to remove the phosphine, arsine, stibine or bismuthine or mixtures thereof from the stream or streams to between about 0 and about 3 ppb. If the non-hydrocarbon gas stream or petroleum hydrocarbon gas stream includes carbon dioxide, hydrogen sulfide, or a mixture thereof, the carbon dioxide, the hydrogen sulfide, or the mixture of the two, should be removed prior to contacting with soda lime.

Our invention will be illustrated by the following specific examples:

EXAMPLE I

Solid 6 mesh soda lime was placed in a tower to a depth of five (5) feet over a bed of alumina balls for support. The tower is 6.5 feet in diameter. A 110° F., 135 lbs/sq inch petroleum hydrocarbon stream flowing at 8000 lbs/hr and having previously $C_1-C_5$ hydrocarbons was contaminated with over 100 ppb arsine. The stream had a free water concentration of less than 1 mole %. The temperature of the hydrocarbon stream was raised to 140° F. Subsequently, the elevated temperature hydrocarbon stream is passed through the soda lime tower such that the contact time of the soda lime with the 140° F. hydrocarbon stream is about 12 seconds. The outlet hydrocarbon stream from the soda lime tower was examined for arsine content and was found to be about 2.0 ppb.

EXAMPLE II

Repeat Example I but contaminate the hydrocarbon stream with phosphine, then with stibine, and then with bismuthine, and find similar results as in Example I.

EXAMPLE III

Repeat Example I but vary the arsine contamination in 100 ppb increments up to 1000 ppb and find similar results.

EXAMPLE IV

Repeat Example I but utilize a tower having slurry soda lime that has been pretreated with about 10 wt% of potassium nitrite. When the hydrocarbon stream is percolated therethrough after the free water concentration is removed, similar results are found.

EXAMPLE V

Repeat Example I with a gas stream as previously described and find similar results.

EXAMPLE VI

Three (3) 6½ ft. diameter×33′0″ long vessels (previously used as process dryers) were commissioned for use in arsine removal service. The vessels were each designed with an eight (8) foot bed of soda lime, so that when a mixed-hydrocarbon refinery stream containing up to 600 parts per billion (volume) of arsine passed downward through the bed, the arsine reacted and a stream containing less than 3 ppb arsine exited the particular bed in service.

The refinery stream being treated for arsine removal contained a significant amount of $CO_2$ and $H_2S$, which first were removed by amine and caustic scrubbing. This is necessary because soda lime will also react with $CO_2$ and $H_2S$, and will rapidly become spent via removal of these two components rather than being available for reaction with arsine.

The refinery stream was passed through a vapor dryer after exiting from its caustic scrubber in order to lower the free concentration below 10 ppm. This was deemed necessary to prevent free water from entering the soda lime bed(s) and inhibiting the arsine removal reaction.

The pre-scrubbed, heated vapor was passed through one or more of the soda lime packed vessels for arsine removal. When the vapor exited the vessels and was analyzed for arsine concentration, it was found to be about 1 ppb.

While the present invention has been described herein with reference to particular examples and embodiments thereof, a latitude of modification, various changes and substitutions are intended in the foregoing disclosure, and it will be appreciated that in some instances some features of the invention will be employed without a corresponding use of other features without departing from the scope of the invention as set forth.

We claim:

1. A method for removing a hydride of an element selected from the group consisting of phosphorous, arsenic, antimony, bismuth, or mixtures thereof from a petroleum hydrocarbon stream primarily having $C_1-C_5$ hydrocarbons and hydrogen, or from a non-hydrocarbon gas stream including a gas selected from the group consisting of nitrogen, oxygen, carbon monoxide, air, and a gas or gases of Group O, or mixture of the gases thereof; or a mixture of the hydrocarbon stream and the non-hydrocarbon gas stream; the method comprising the steps of:

(a) raising the predetermined known temperature of the hydrocarbon stream of the non-hydrocarbon gas stream or the mixtures of the two streams to between 120° F. and about 170°; and (b) contracting for at least 8 seconds the effluent of step (a) with a soda lime bed formation means having at least a five (5) foot length.

2. The method of claim 1 wherein the concentration of the hydride of the element selected from the group consisting of phosphorous, arsenic, antimony, bismuth, or mixtures thereof, is reduced to less than about 3 ppb.

3. The method of claim 1 wherein said soda lime is in a solid state and has a particle size of 4 to 8 mesh.

4. The method of claim 1 wherein said soda lime is in a slurry state and said method additionally comprises adding from about 1 wt% to about 25 wt% of a compound selected from the group consisting of potassium nitrite and sodium nitrite, or mixtures thereof, to the slurry soda lime.

5. The method of claim 1 wherein the flow rate of said hydrocarbon stream or said non-hydrocarbon gas stream or a mixture of the two streams is from about 150 lbs/hr/sq. ft. of soda lime bed to about 450 lbs/hr/sq. ft. of soda lime bed, and the pressure of said hydrocarbon stream or said non-hydrocarbon gas stream or the mixture of the two streams is from about 125 lbs/sq inch absolute to about 200 lbs/sq inch absolute.

6. The method of claim 1 wherein said non-hydrocarbon gas stream additionally comprises a gas selected from the group consisting of carbon dioxide, hydrogen sulfide, or a mixture thereof; and said method additionally comprises removing said carbon dioxide, hydrogen sulfide, or the mixture thereof prior to contacting with said soda lime.

7. A method for removing a hydride of an element selected from the group consisting of phosphorous, arsenic, antimony, bismuth, or mixtures thereof from a petroleum hydrocarbon stream primarily having $C_1$–$C_5$ hydrocarbons and hydrogen, or from a non-hydrocarbon gas stream including a gas selected from the group consisting of nitrogen, oxygen, carbon monoxide, air, and a gas or gases of Group O, or mixture of the gases thereof; or a mixture of the hydrocarbon stream and the non-hydrocarbon gas stream; the method comprising the steps of:

(a) reducing the free water concentration of the hydrocarbon stream or the gas stream or the mixtures of the two streams by passing said stream or streams through a vapor dryer means; and (b) contacting for at least 8 seconds the effluent of step (a) with a soda lime bed formation means having at least a five (5) foot length.

8. The method of claim 7 wherein said free water concentration is reduced from the range of about 100 ppm to 1000 ppm to a range from about 1 ppm to 20 ppm.

9. The method of claim 7 wherein the concentration of the hydride of the element selected from the group consisting of phosphorous, arsenic, antimony, bismuth, or mixtures thereof, is reduced to less than about 3 ppb.

10. The method of claim 7 wherein said soda lime is in a solid state and has a particle size of 4 to 8 mesh.

11. The method of claim 7 wherein said soda lime is in a slurry state and said method additionally comprises adding from about 1 wt% to about 25 wt% of a compound selected from the group consisting of potassium nitrite and sodium nitrite, or mixtures thereof, to the slurry soda lime.

12. The method of claim 7 wherein the flow rate of said hydrocarbon stream or said non-hydrocarbon gas stream or a mixture of the two streams is from about 150 lbs/hr/sq. ft. of soda lime bed to about 450 lb/hr/sq. ft. of soda lime bed, and the pressure of said hydrocarbon stream or said non-hydrocarbon stream or the mixture of the two streams is from about 125 lb/sq. inch absolute to about 200 lbs/sq. inch absolute.

13. The method of claim 7 wherein non-hydrocarbon gas stream additionally comprises a gas selected from the group consisting of carbon dioxide, hydrogen sulfide, or a mixture thereof; and said method additionally comprises removing said carbon dioxide, hydrogen sulfide, or the mixture thereof prior to contacting with said soda lime.

* * * * *